Nov. 29, 1932. O. C. CORDREY ET AL Plant Pat. 46
STRAWBERRY
Filed March 31, 1932
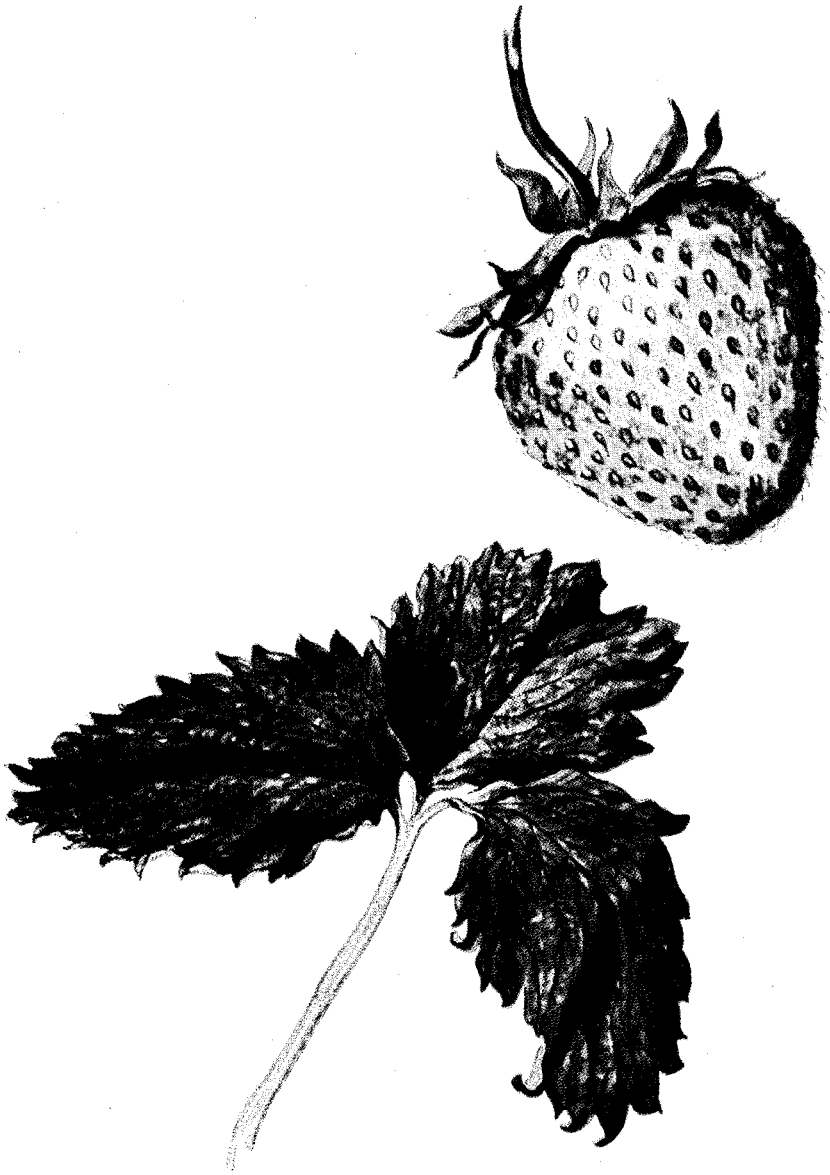
Inventors
Hannah E. Cordrey, and
Charles M. Freeman, for
The Eastern Shore Trust Co.,
Administrators of the estate of
Oliver C. Cordery, deceased.
Ernest W. Townsend.
Orville M. Kile
ATTORNEY Patented Nov. 29, 1932 Plant Pat. 46

UNITED STATES PATENT OFFICE

OLIVER C. CORDREY, DECEASED, LATE OF SALISBURY, MARYLAND, BY HANNAH E. CORDREY AND EASTERN SHORE TRUST COMPANY, ADMINISTRATORS, OF SALISBURY, MARYLAND, AND ERNEST W. TOWNSEND, OF SALISBURY, MARYLAND, ASSIGNORS TO SAID ERNEST W. TOWNSEND

STRAWBERRY

Application filed March 31, 1932. Serial No. 602,383.

Our invention relates to improvements in early commercial strawberries of the type known as "perfect." The object of our invention is to provide an early ripening strawberry in which is combined certain desirable qualities of other strawberries, particularly the Gandy, Premier and Blakemore, as well as possessing certain other desirable characters.

Our new variety of strawberry is the result of a scientific cross between the varieties Howard 17, otherwise known as Premier, and the Gandy. The original cross fertilization work was done by Mr. Cordrey, the first named joint inventor, and the resulting seed was also planted by Mr. Cordrey. The box of approximately 100 seedlings of unknown qualities was then turned over to Mr. Townsend, the second named joint inventor, who transplanted the seedlings, cared for them and studied their characteristics. The new variety which is the subject of this patent application was first discovered by the second named joint inventor in the spring of 1925. The first named joint inventor gave no further attention to the study, selection, development or propagation of these seedlings after they were given to Mr. Townsend. All matters of study, selection, development and asexual propagation of this variety were carried out by Mr. Townsend without the aid, supervision or even the knowledge of Mr. Cordrey. Only the one seedling of the group of 100 young plants proved promising and all the rest were destroyed. The second named joint inventor has consistently developed, tested and propagated this new variety since 1925 and in the spring of 1931 first offered plants of this variety to the public.

The accompanying illustration shows in full color, enlarged, a fully ripened strawberry and foliage (natural size) of this new variety. The foliage is slightly wilted, having been cut 36 hours by the time the artist finished.

The following is a description of this new variety of strawberry:

*Berry:*—bluntly conic with occasional berry flat sided or fan shaped, resembling the Gandy variety; medium large in size; color a rich bright red, even color all over; ripens uniformly, no white tips or light rings at crown as often found in the Blakemore variety; seeds yellow to greenish yellow, small, extending slightly beyond surface of the berry; flesh, pink slightly streaked with white, firm, tender, rarely with cavity, juicy; flavor is sweet and has a distinctive sprightly, aromatic or permeating character.

*Calyx:*—slightly reflexed, commonly 10 sepals in two rows, one or two sepals usually notched, and together forming a heavy calyx easily plucked which facilitates "capping." The blossoms are well supplied with pollen, making this an ideal variety to plant with "imperfect" varieties of the same blooming season. This new variety is classed as an early strawberry ripening at about the same time as Premier.

*Plant:*—large, strong, vigorous grower, having healthy-looking dark green foliage, is rust resistant, leaves deeply serrated, usually having 20 to 26 points per leaf. Each plant puts out many short, strong fruiting stems which makes the variety a very heavy producer. It has a heavy crown and very full root system.

The more important features which we believe distinguish our new strawberry variety from other known early varieties are:

1. Resembles the Gandy in size, shape and outside color but ripens at about the same time as the Premier, being about 10 days earlier than the Gandy.

2. Produces heavier crop than most early varieties, being equal or better in this respect than the well known Premier (Howards 17).

3. Has red color of Gandy variety on outside of berry but has the pink color of Premier variety inside.

4. Produces heavier and larger plants and the calyx is heavier than in most early varieties.

5. Has unusual and pleasing flavor and aroma, not found in other early varieties.

We claim:

The variety of strawberry as herein described and illustrated, characterized by its heavy plant growth, strong producing qualities, its early ripening of berries of superior color and shape, and having a distinctive sprightly, aromatic flavor.

ERNEST W. TOWNSEND.
HANNAH E. CORDREY,
CHARLES M. FREEMAN, [L. S.]
*For the Eastern Shore Trust Co., Administrators of the Estate of Oliver C. Cordrey, Deceased.*